(12) United States Patent
Madore et al.

(10) Patent No.: US 6,353,752 B1
(45) Date of Patent: Mar. 5, 2002

(54) REDUCED FIELD-OF-VIEW METHOD FOR CINE MAGNETIC RESONANCE IMAGING

(75) Inventors: Bruno Madore, Redwood City; Norbert J. Pelc, Los Altos, both of CA (US)

(73) Assignee: Board of Trustees of the Leland Standford Junior University, Palo Alto, CA (US)

(*) Notice: Subject to any disclaimer, the term of this patent is extended or adjusted under 35 U.S.C. 154(b) by 0 days.

(21) Appl. No.: 09/312,027

(22) Filed: May 14, 1999

(51) Int. Cl.[7] .............................................. A61B 5/055
(52) U.S. Cl. ........................ 600/410; 324/307; 324/309
(58) Field of Search ................................ 600/407, 410, 600/411, 417, 415, 420, 429; 324/307, 309, 310

(56) References Cited

U.S. PATENT DOCUMENTS

| | | | | |
|---|---|---|---|---|
| 4,710,717 A | * | 12/1987 | Pelc et al. | 128/653.2 |
| 5,615,677 A | * | 4/1997 | Pelc et al. | 128/653.2 |
| 5,653,233 A | * | 8/1997 | Pelc et al. | 128/653.2 |
| 5,697,370 A | * | 12/1997 | Pelc et al. | 128/653.2 |
| 5,873,825 A | * | 2/1999 | Mistretta et al. | 128/653.2 |

OTHER PUBLICATIONS

Xiaoping Hu, Todd Parish, "Reduction of Field of View for Dynamic Imaging", MRM 31:691–694 (1994).
Jill O. Fredrickson, Norbert J. Pelc, "Temporal Resolution Improvement in Dynamic Imaging", MRM 35:621–625 (1996).
Bruno Madore, Gary H. Glover and Norbert J. Pelc, "UNaliasing by Fourier–encoding the Overlaps using the temporaL Dimension (UNFOLD), applied to cardiac imaging and fMRI", MRM 1–62 (Spring 1999).

Gerald w. Lenz, E. Mark Haacke, and Richard D. White, "Retrospective Cardiac Gating: A Review of Technical Aspects and Future Directions", MRM vol. 7, No. 5 445–455 (1989).

* cited by examiner

*Primary Examiner*—Marvin M. Lateef
*Assistant Examiner*—Talaya James
(74) *Attorney, Agent, or Firm*—Townsend and Townsend and Crew LLP; Henry K. Woodward

(57) ABSTRACT

In some dynamic applications of MRI, only a part of the field-of-view (FOV) actually undergoes dynamic changes. A class of methods, called reduced-FOV (rFOV) methods, convert the knowledge that some part of the FOV is static or not very dynamic into an increase in temporal resolution for the dynamic part, or into a reduction in the scan time. Although cardiac imaging is an important example of an imaging situation where changes are concentrated into a fraction of the FOV, the rFOV methods developed up to now are not compatible with one of the most common cardiac sequences, the so-called retrospective cine method. The present work is a rFOV method designed to be compatible with cine imaging. An increase by a factor n in temporal resolution or a decrease by n in scan time is obtained in the case where only one $n^{th}$ of the FOV is dynamic (the rest being considered static). Results are presented for both Cartesian and spiral imaging.

18 Claims, 5 Drawing Sheets

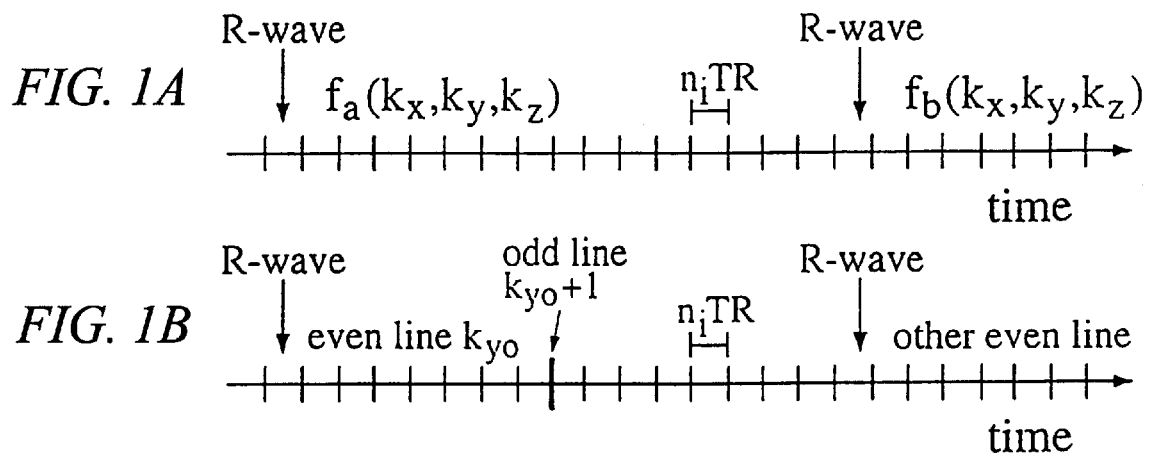
FIG. 1A
FIG. 1B
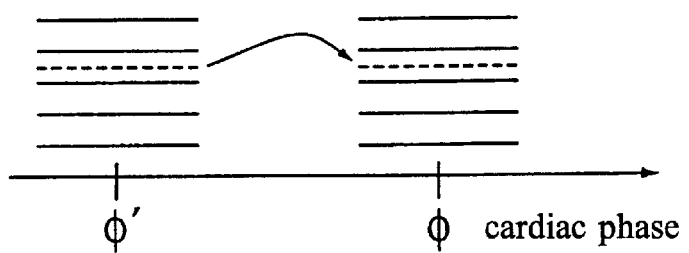
FIG. 2

REDUCED FIELD-OF-VIEW METHOD FOR CINE MAGNETIC RESONANCE IMAGING

STATEMENT AS TO RIGHTS TO INVENTIONS MADE UNDER FEDERALLY SPONSORED RESEARCH AND DEVELOPMENT

The U.S. Government has rights in this invention pursuant to NIH grant P41RR09784 to Stanford University.

BACKGROUND OF THE INVENTION

This invention relates generally to magnetic resonance imaging (MRI), and more particularly the invention relates to imaging a dynamic object in which a field of view includes both a dynamic portion and a static portion during a motion cycle. The invention and background will be described with reference to publications listed in the attached appendix.

Several MRI applications involve imaging a dynamic object to resolve its temporal behavior [1–8]. In such applications, it is often difficult to achieve the desired temporal resolution while maintaining the required spatial resolution and field-of-view (FOV). Methods have been developed to increase the temporal resolution in the special case where only a fraction of the FOV undergoes fully dynamic changes [9, 12], the rest of the FOV being considered fully static [9, 11], undergoing a cyclic motion [10], or just being 'less dynamic' than the fully dynamic part [12]. Although cardiac imaging is an important example of an imaging application where motion is concentrated into only a part of the FOV, the reduced-FOV (rFOV) methods mentioned above are not compatible with one of the most common cardiac sequences, so-called 'retrospective' cine imaging [1, 2]. Because of the time interpolation involved in cine reconstruction, one cannot change the sampling function from time frame to time frame as is done in [11, 12], or acquire only one or a few full FOV images as is done in [9, 10].

The present invention is a rFOV method designed to be compatible with cine imaging, providing an increase by a factor n in temporal resolution (or a decrease by a factor n in scan time) if only $1/n^{th}$ of the FOV is dynamic, the rest being considered static.

SUMMARY OF THE INVENTION

With the present method, only a fraction of all the k-space 'portions' (e.g. lines) need to be acquired multiple times over a full cardiac cycle (instead of all the k-space 'portions', as in normal CINE imaging). It is shown that if only one $n^{th}$ of the FOV is dynamic, only one $n^{th}$ of the k-space 'portions' need to be acquired multiple times. The remaining fraction ((n−1)/n) of the k-space 'portions' can be acquired only once, leading to an increase by about a factor n in temporal resolution or a decrease by about n in scan time. Using the data acquired multiple times, along with the assumption that only one $n^{th}$ of the FOV is dynamic, it is shown that values for the 'portions' acquired only once can be calculated for any cardiac phase. Accordingly, there is no need to acquire this data at multiple cardiac phases. Avoiding the acquisition of such unnecessary data leads to the stated increase in temporal resolution, or decrease in scan time.

The invention and objects and features thereof will be more readily apparent from the following description and appended claims when taken with the drawings.

BRIEF DESCRIPTION OF THE DRAWINGS

FIG. 1 illustrates k-space image signal acquisition.

FIG. 2 illustrates k-space line transfer to complete an image data frame.

Figure Captions

FIG. 1: In a normal cine imaging sequence, a k-space 'portion' $f_a(k_x, k_y, k_z)$ is acquired every $n_iTR$ for a full cardiac cycle (each tick mark on the time axis represents a readout window), where $n_i$ is the number of k-space 'portions' acquired in an interleaved fashion within a given heartbeat. Different k-space portions (like $f_b$) are acquired during other heartbeats. b) With the present method, only one $n^{th}$ of the k-space 'portions' are acquired repeatedly over a full cardiac cycle. For example, in the case of a Cartesian imaging sequence and n=2, all the even $k_y$ lines are acquired multiple times. On the other hand, the odd lines are acquired only once. As shown with the larger tick mark, one acquisition of an even $k_y$ line $k_{yo}$ is replaced by the acquisition of an odd line ($k_{yo}+1$).

FIG. 2: An odd $k_y$ line acquired at some cardiac phase $\phi'$ (dashed line) has to be 'transferred' somehow to $\phi$ where a frame is reconstructed. The text, along with Eqs. 1 and 2, explains how the transfer can be performed. This process is repeated to transfer all the odd lines to all the cardiac phases where a frame is reconstructed.

FIG. 3: Images of a pig's heart acquired with a modified version of the 3D GRE pulse sequence presented in [15], about half an hour after a contrast agent injection (Gadolinium DTPA, 0.3 mMol/kg). The slice shown is located near the center of a 16 slice (interpolated to 32) 3D volume, and 16 cardiac time frames were reconstructed (TR=5.2 ms, TE=1.5 ms, acquired 3D FOV=20×10×8 cm, acquired matrix=256×128×16, the 16 slice encodings are acquired in an interleaved fashion, flip angle=25°, heart rate≈82 bpm, imaging time ≈1 minute 34 seconds). As required by the present method, the sequence was modified to acquire only one copy of the odd $k_y$ lines (while even $k_y$ lines were sampled throughout a cardiac cycle). a) and b) are reconstructed using only the even $k_y$ lines (which can be temporally interpolated to any phase in the cardiac cycle), while c) and d) are reconstructed using the proposed method (reconstructed in-plane FOV=20 by 20 cm). a) and c) are generated at a cardiac phase near systole, while b) and d) are reconstructed near mid-diastole. Note that the aliasing present in a) and b) appears to be corrected in c) and d), without compromising the temporal resolution over the heart.

Figure 3A:
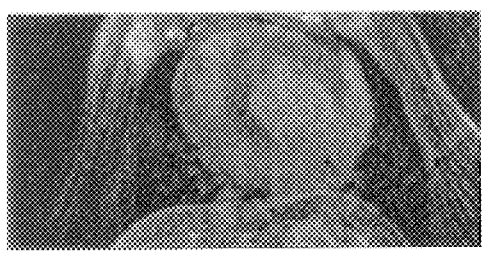
FIG. 3 illustrates MRI images in accordance with the prior art and with the present invention.
Figure 3B:
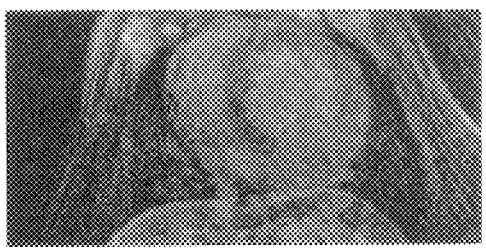
Figure 3C:
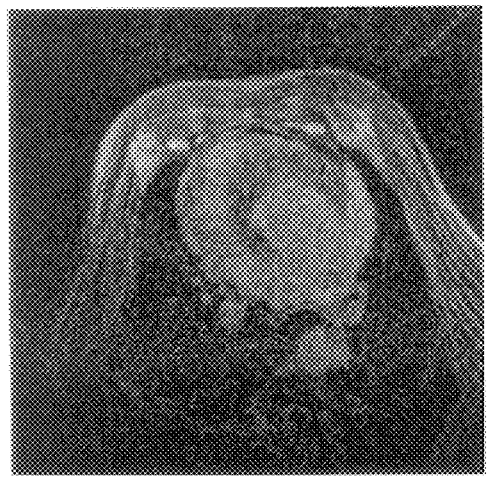
Figure 3D:
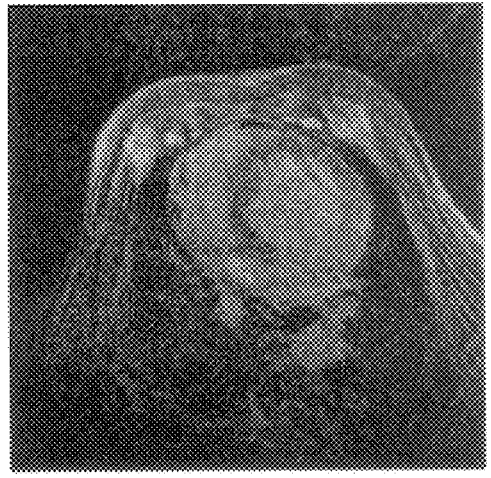
Figure 4:
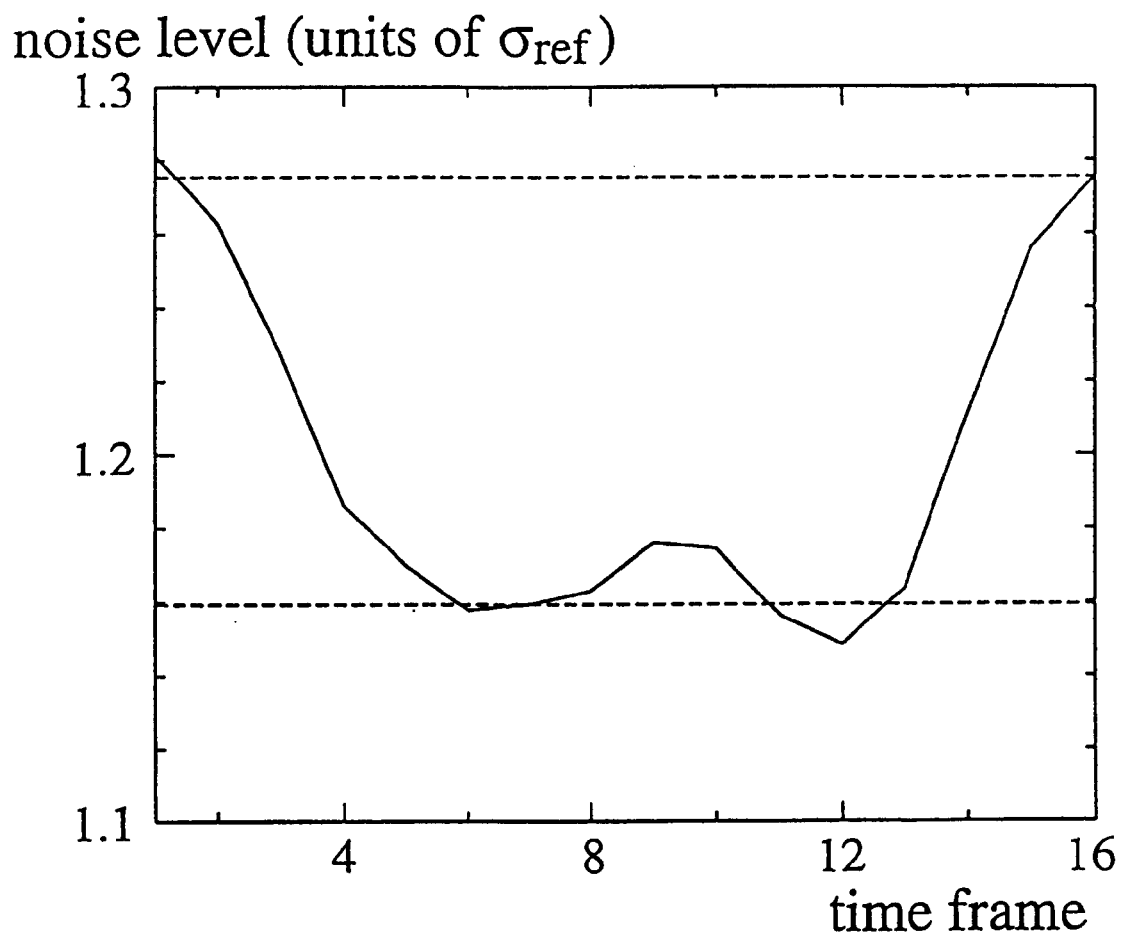
FIG. 4 illustrates noise level in MRI frames using the invention.

FIG. 4: A small, static phantom was imaged using same imaging parameters as for the results in FIG. 3 (using an ECG simulator set at 75 bpm), and the noise level in the dynamic part of the reconstructed images is plotted (in units of $\sigma_{ref}$, defined in Appendix 1) as a function of frame number (i.e. cardiac phase). The upper dashed straight line represents the noise level expected through Eq. 5 for frames at early or late cardiac phases. The lower straight dashed line shows the noise level expected through Eq. 10 for intermediate cardiac phases. With a heartbeat roughly every 800 ms, 16 slices interleaved and a TR 5.2 ms, about 10 time points are acquired every heartbeat. The first and the last time points are not available for the acquisition of an odd line in order to, respectively, depict systole as well as possible and avoid missing the acquisition of an odd line if arrhythmia occurs. Accordingly, N≈8 time points are available for the acquisition of an odd $k_y$ line, in Eq. 10. The solid line represents the measured noise level; notice that as expected, the measured noise is close to the upper straight dashed line for early and late cardiac phases, while it is close to the lower straight dashed line for intermediate cardiac phases.

FIG. 5: Images of a volunteer's heart acquired with a modified version of a 2D spiral cine imaging sequence [16] during breath holding. (16 cardiac time frames were reconstructed, TR=50 ms, TE=6.5 ms, 10 spiral interleaves were dynamically acquired while 10 were acquired only once, the dynamically acquired FOV has a radius of 14 cm, reconstructed matrix=256 by 256, the reconstructed FOV has a radius of 28 cm, flip angle=30°, heart rate≈64 bpm, imaging time≈9.5 seconds). a) and b) are reconstructed using only the 10 dynamically acquired spiral interleaves, while c) and d) are reconstructed using the proposed method. a) and c) are generated at a cardiac phase near systole, while b) and d) are reconstructed near mid-diastole. The aliasing present in a) and b) appears to be corrected in c) and d), without compromising the temporal resolution over the heart.

FIG. 6: The tick marks on the cardiac phase axis represent readout windows. At some cardiac phase $\phi'$, one of the multiple acquisitions of a k-space portion is replaced by the single acquisition of a different portion. As a frame is reconstructed at $\phi$, the present method involves interpolating (e.g. linearly) in time both at $\phi$ and $\phi'$ the k-space portions acquired multiple times. The readout windows used for the interpolation are highlighted by a dashed ellipse. Depending on the relative position of $\phi$ and $\phi'$, the two interpolations can use completely different readout windows (a), share one readout window (b), or share both readout windows (c). The situation depicted in (a), (b) and (c) would give rise to different noise levels in the dynamic part of reconstructed images, as described respectively by Eq. 5, 6, and 7. As depicted in (a), a weight a and (1−a) is given to the two acquisitions involved in the interpolation at $\phi$, while weights −b and −(1−b) are given to the acquisitions involved in the interpolation at $\phi'$ (the negative sign comes from Eq. 3 where $h(M_{\phi'})$ is subtracted). The factor n(n−1) is due to interpolation in k-space, as explained in the first part of Appendix 2.

Figure 7:
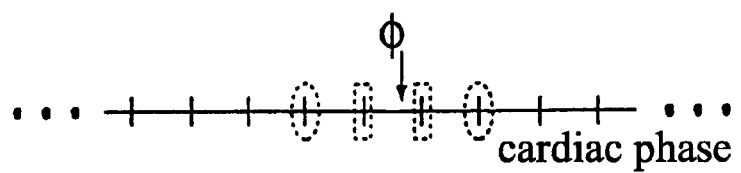
FIG. 7 illustrates MRI images using k-space data transfers as shown in FIG. 6.

FIG. 7: With the proposed implementation, the replacement described in the text occurs at an intermediate cardiac phase. In the example depicted here, any one of N (=9 in the drawing) acquisitions could be chosen, with an equal probability. Suppose that a time frame is reconstructed at $\phi$. The data interpolated at $\phi$ would come from the two readout windows highlighted by a dashed rectangular box. Suppose for a moment that the replaced acquisition (located by definition at $\phi'$) is one of the two readout windows highlighted by a dashed ellipse. The interpolation at $\phi'$ would then involve one of the readout windows highlighted with a rectangle, and one other readout window. This scenario, where the interpolation at $\phi$ and $\phi'$ use a common readout window, has a probability $P_2=2/N$ of happening. Now suppose that the replaced acquisition is one of the two readout windows highlighted by a rectangular box. The interpolation at $\phi$ is now performed using the other (non-replaced) acquisition highlighted with a box, and one highlighted with an ellipse. The replaced acquisition (at $\phi'$) also lies between the two same readout windows, and the interpolation at $\phi'$ involves the same data as the interpolation at $\phi$. This situation has a probability $P_3=2/N$ of happening. In any other case ($P_1=(N-4)/N$), the interpolation at $\phi$ and $\phi'$ involve different readout windows.

DETAILED DESCRIPTION OF THE ILLUSTRATIVE EMBODIMENT

The basic aspects of Magnetic Resonance Imaging (MRI), or imaging using NMR signals, is by now well understood. Spatial information is encoded into the acquired MRI signals using magnetic field gradients that are controlled by a pulse sequence program. Thus, each acquired signal is associated with a spatial encoding parameter. Generally, each acquired data point represents a sample of the Fourier transform of the imaged object. The "space" in which the Fourier transform samples, are defined is called "k space". Often, the k space samples arc on a Cartesian grid and each pulse sequence repetition collects samples on one line in k space. An important spatial encoding parameter in this case is the so-called phase encoding amplitude. In another MRI method, the samples collected in one pulse sequence repetition fall on spiral paths in k space, and k space is filled using multiple rotations of this spiral path. An important spatial encoding parameter in this case is the angular rotation of the spiral path.

Suppose that $f_i(k_x, k_y, k_z)$ is the $i^{th}$ portion of the k-space matrix to be acquired (e.g. $f_i(k_x, k_y, k_z)$ can be a k-space line or a spiral interleaf). FIG. 1a depicts a normal cine acquisition [1,2]. Each tick mark on the time axis represents a readout window. For a full cardiac cycle (i.e. the time between two R-waves), a portion $f_a(k_x, k_y, k_z)$ of the k-space matrix is acquired repeatedly. A different portion $f_b(k_x, k_y, k_z)$ is acquired during the next cardiac cycle. Other portions of the k-space matrix maybe acquired in an interleaved fashion between the $f_a(k_x, k_y, k_z)$ or the $f_b(k_x, k_y, k_z)$ acquisitions, or in different cardiac cycles. Knowing the timing of the R-waves, the time axis is converted into cardiac phase. Using (e.g. linear) interpolation, the $f_i(k_x, k_y, k_z)$ are evaluated at the phase values where reconstructed frames are desired.

FIG. 1b depicts the acquisition process for the present method. As in FIG. 1a, a given $f_i(k_x, k_y, k_z)$ is acquired repeatedly during a cardiac cycle. However, only $1/n^{th}$ of the $f_i(k_x, k_y, k_z)$ are acquired in this fashion. For simplicity, FIG. 1b (as well as most of the remainder of the Detailed Description) describes the present method for the special case of a 2D Cartesian imaging sequence ($f_i(k_x, k_y, k_z)$ is simply a $k_y$ line) and n=2 (half the FOV is considered static). In this case, half the $k_y$ lines (let's say the even ones) are acquired in a way similar to conventional cine. On the other hand, the odd $k_y$ lines are not acquired repeatedly over a full cardiac cycle; instead a single view is acquired in place of a single even $k_y$ view, as depicted with the larger tick mark on the time axis in FIG. 1b. For respiration compensation techniques [13] to work properly when combined with the present method, the odd $k_y$ line acquired once and the even line it, replaces should correspond to similar respiratory phases, e.g. close to each other in k-space for a 'low frequency' sort pattern [14] (as in FIG. 1b, where the phase-encode value is changed from ($k_{yo}$ to $k_{yo}$+1)).

For reconstruction, the even $k_y$ lines are interpolated in time as usual. It is assumed that the missing time point, (where an even $k_y$ sample was replaced by an odd $k_y$ line), does not seriously degrade the ability to interpolate the even lines to the desired phases in the cardiac cycle. On the other hand, interpolation is not possible for the odd $k_y$ lines since only one time point is available. The challenge consists in calculating the odd lines at the cardiac phases where reconstructed frames are desired, knowing their value only at the single cardiac phase where they have been acquired. The benefits of the method are as follow. Since the amount of data to acquire is reduced by a factor two, the number of heartbeats required for data collection can be halved (reducing scan time by a factor two). The present method can emulate the no-phase wrap option, if half the FOV can be considered static (without the factor two time penalty associated with no-phase wrap). Alternatively, temporal resolution can be increased by a factor two in the case where a segmented k-space cine sequence is used. Such a sequence allows a trade-off between scan time and temporal resolution by interleaving the acquisitions of $N_{int}$ different k-space portions, reducing the number of required heartbeats (and scan time) by a factor $N_{int}$ while reducing temporal resolution to $N_{int}$TR (instead of TR, as with conventional cine methods). As implemented on a segmented k-space sequence, the present method could either reduce the number of interleaved acquisitions (increase temporal resolution) or reduce the number of heartbeats required for data acquisition (reduce scan time).

FIG. 2 shows a frame being reconstructed at some desired cardiac phase $\phi$. As mentioned above, the even $k_y$ lines can be interpolated at $\phi$. However, to reconstruct a time frame one must also evaluate all the odd lines for this phase value. For example, a given odd $k_y$ line acquired at cardiac phase $\phi'$ has to be somehow 'transferred' from $\phi'$ to $\phi$(arrow and dashed lines in FIG. 2). The following paragraphs explain how this transfer can be done. The same process can be used to transfer all the odd $k_y$ lines to every cardiac phase where a frame is desired.

In a first step, all the even $k_y$ lines are interpolated in time (or equivalently, cardiac phase) to generate k-space data frames both at $\phi$ and $\phi'$. If reconstructed, these would produce spatially aliased images. Let the k-space made of the even lines at $\phi$ be $K_{half}(k_x, k_y)$ and the one at $\phi'$ be $K'_{half}(k_x, k_y)$. Let's also define $\Delta_{half}$ as the difference in the even $k_y$ lines between $\phi$ and $\phi'$:

$$\Delta_{half}(k_x, k_y) = K_{half}(k_x, k_y) - K'_{half}(k_x, k_y) \quad (1)$$

Because $\Delta_{half}$ has only even $k_y$ lines (as $K_{half}$ and $K'_{half}$), it might be expected to give rise, through a Fourier transform (FT), to an image corrupted by aliasing. However, it is assumed that half the FOV is static while the other half is allowed to be dynamic; accordingly, all the k-space information portraying the static material disappears through the subtraction in Eq. 1. An FT of $\Delta_{half}$ would therefore show only the signal coming from the dynamic region. If this dynamic region is centered along the phase-encoding direction (either at the acquisition stage or through post-processing), then $\Delta_{half}$ does not contain any aliased signal (since what would have been aliased, the static portion of the imaged object, was removed by the subtraction in Eq. 1). Since no aliasing is present in the FT of $\Delta_{half}$, the sampling along $k_y$ is "sufficient" (respects the Nyquist criterion), and from the sampling theorem $\Delta_{half}$ can equivalently be represented using only the even $k_y$ lines, only the odd ones, or both. By (sinc) interpolation along $k_y$, a full k-space matrix $\Delta(k_x, k_y)$ (with both odd and even $k_y$ lines) can be generated from the matrix $\Delta_{half}(k_x, k_y)$ (which is made of only the even lines). In the present Cartesian 2D example with n=2, this interpolation can be done using a FT of $\Delta_{half}$, zero-padding by a factor 2, and an inverse FT. In more general cases, more general methods would be required to interpolate in k-space (as described in Appendix 2).

$\Delta(k_x, k_y)$ contains information on how any line of the full k-space matrix changes between $\phi$ and $\phi'$ due to changes in the dynamic region. Accordingly, if $f_{\phi'}(k_x, k_{yo})$ represents a line of data measured at $k_y = k_{yo}$ and at some cardiac phase $\phi'$, this $k_y$ line can be transferred to another phase $\phi$ using:

$$f_\phi(k_x, k_{yo}) = f_{\phi'}(k_x, k_{yo}) + \Delta(k_x, k_{yo}) \quad (2)$$

Thus, to reconstruct images from the measured data, the even $k_y$ lines are interpolated in time in a way similar to conventional cine, while the odd $k_y$ lines (which are acquired only once) are transferred one by one using Eq. 2, from the cardiac phase where they have been acquired to the cardiac phases where they are needed to reconstruct a frame. Note that the interpolation that generates $\Delta$ from $\Delta_{half}$ need not produce all the odd $k_y$ lines if only the line at $k_y = k_{yo}$, is needed.

The description above can be generalized to n>2 in the following way. If only one $n^{th}$ of the FOV is dynamic, then $K_n$ and $K'_n$ (in place of $K_{half}$ and $K'_{half}$ in Eq. 1) contain only one $n^{th}$ of all the $k_y$ lines that would be required to obtain a full (non-aliased) FOV. They are subtracted to produce $\Delta_n$. Since all the static material disappears in the subtraction, $\Delta_n$ does not contain any aliasing. Interpolating $\Delta_n$ by a factor n gives $\Delta$, which is used as shown in Eq. 2 to transfer all the lines that have been acquired only once (instead of repeatedly over a full cardiac cycle), from the cardiac phase where they have been acquired to the phase where they are needed for reconstruction.

Furthermore, the description provided in this section can be generalize(d to non-Cartesian imaging methods. If acquiring only one $n^{th}$ of the k-space data reduces the FOV by a factor n (as is the case in spiral imaging for example), then the FT of the k-space matrices on the right-hand side of Eq. 1 are corrupted by an n-fold aliasing. On the other hand, because all the static material is removed by subtraction, the FT of the left-hand side of Eq. 1 is an image the size of the dynamic region, free of aliasing. Because the Nyquist criterion is respected in this difference image, the missing k-space data (e.g. missing spiral interleaves) can be obtained by interpolation. Once a full $\Delta(k_x, k_y)$ is interpolated, the k-space portions (e.g. spiral interleaves) that have been acquired only once can be transferred from the cardiac phase where they have been acquired to the cardiac phase where they are needed, using an equation similar to Eq. 2.

Eq. 3 in Appendix 1 is a combination of Eq. 1 and Eq. 2. Eq. 3 does not make assumptions on the value of n or on the choice of imaging sequence. This equation is used in Appendix 1 and Appendix 3,respectively, to derive the SNR properties and to present an efficient processing algorithm for the present methods.

In the next section, results are presented where the present method reduces scan time by a factor two in a 3D Cartesian as well as a 2D spiral acquisition.

Cartesian Imaging

A cardiac cine study [1,2] was performed on a pig using a modified version of the 3D GRE pulse sequence presented in [15] operating on a Signa 1.5 T Echospeed MRI system (GE Medical Systems, Milwaukee, Wis.). Contrast agent (Gadolinium DTPA, 0.3 mMol/kg) was injected about thirty minutes before the 3D Cartesian cine scan was performed. A total of 16 cardiac phases were reconstructed, and 16 slices were acquired (interpolated to 32 by zero-filling). Half the $k_y$ lines (even ones) were acquired repeatedly over a full cardiac cycle (n=2, the dynamic FOV is ½ the full FOV), while the other half were acquired only a single time by replacing one of the acquisitions of an even $k_y$ line by the acquisition of an odd $k_y$ line. Typically, 9 time points could be acquired during a heartbeat. To obtain as much dynamic information as possible during systole, the first time point in any given heartbeat consists of an even $k_y$ line (this time point could not be replaced by the acquisition of an odd line). Similarly, to avoid the situation where the next R-wave would occur before the required odd line is acquired, the replacement cannot be scheduled in the last 10% (~1 time point) of the cardiac cycle. The replacement occurs at one of the remaining ~7 intermediate time points (random pick with flat probability density function). FIGS. 3a and 3b show a slice near the center of the 3D volume, close to systole (FIG. 3a) and in mid-diastol (FIG. 3b). These images were reconstructed in a conventional way using the dynamic even $k_y$ lines (the odd lines were dismissed). FIGS. 3c and 3d show the images as reconstructed using the present method. Note that the aliasing, problem seen in FIGS. 3a and 3b is substantially corrected in FIGS. 3c and 3d.

To assess the SNR properties of the present method, a small static phantom was imaged with the same imaging parameters as in FIG. 3, using an ECG simulator set at 75 bpm. The noise level was measured and compared to the predictions of Appendix 1. First, $\sigma_{ref}$ (as defined in Appendix 1) was measured using the acquired even $k_y$ lines. Then, the noise level in the static region was measured to be $0.78\sigma_{ref}$ (theoretical value $0.79\sigma_{ref}$ from the square-root of Eq. 4, with n=2). FIG. 4 shows the noise level in the dynamic part in units of $\sigma_{ref}$, as a function of cardiac phase. The upper dashed straight line shows the noise level expected from Eq. 5 for the early and late cardiac phases ($1.27\sigma_{ref}$), while the lower dashed straight line shows the prediction of Eq. 10 for N=number of intermediate frames where the replacement can occur $\approx 8(1.16\sigma_{ref})$. The solid line represents the measured noise level; as expected, this line is close to the upper dashed straight line for early and late cardiac phases, while it is close to the lower dashed straight line for intermediate cardiac phases.

Spiral imaging

Figure 5A:
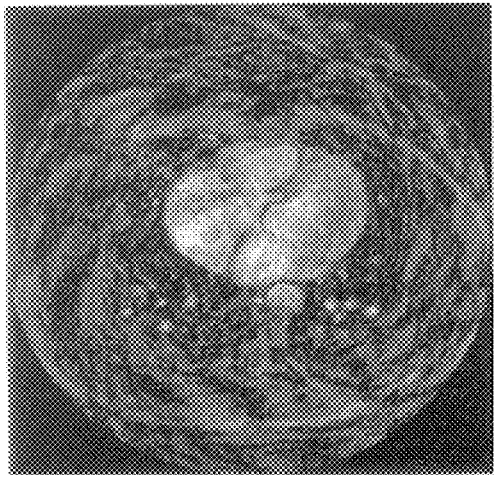
FIG. 5 illustrates MRI frame reconstruction near systole and mid-diastole.
Figure 5B:
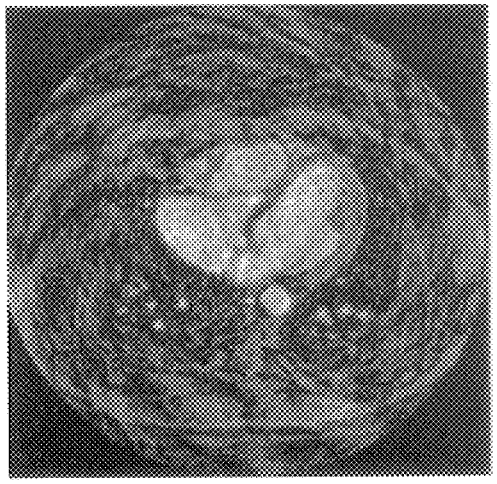
Figure 5C:
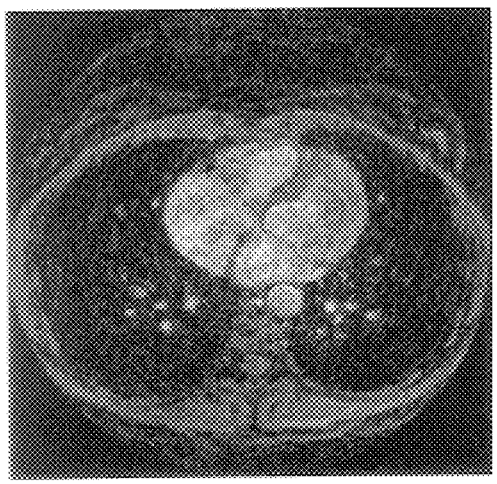
Figure 5D:
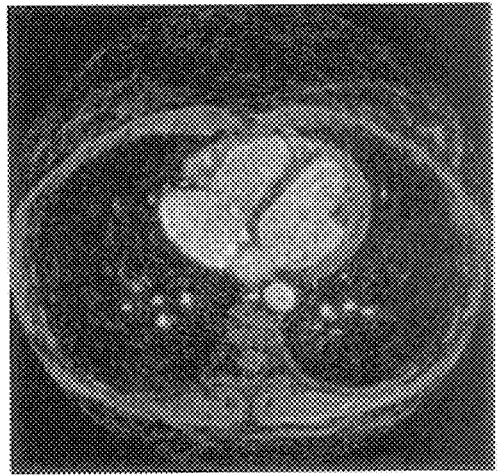

The present method was also implemented on a 2D cine spiral imaging pulse sequence [16]. A single slice was imaged through the heart of a volunteer (no injection of contrast agent, TR of 50 ms). Half of the spiral interleaves were dynamically acquired, while the others were obtained only a single time. Typically, about 18 time points could be acquired within a heartbeat. Similarly to the Cartesian case, the first 4 and the last 10% (about 2 time points) were made unavailable for the single acquisition of a different spiral interleaf. Hence, this replacement occurred at one of the remaining ~12 intermediate time frames (random pick with flat probability density function). Frames that have been reconstructed for cardiac phases near systole and mid-diastole arc shown, respectively, in FIGS. 5a and 5c and in FIGS. 5b and 5d. FIGS. 5a and 5b are reconstructed using only the dynamically acquired interleaves, while FIGS. 5c and 5d are reconstructed using the proposed method. Note that the heart's edges appear sharp in the treated images (no loss of temporal resolution) while the aliasing problem seen in FIGS. 5a and 5b is substantially corrected in the treated images shown in FIGS. 5c and 5d.

Discussion

The present cine method assumes that only $1/n^{th}$ of the FOV is dynamic, while the rest is considered static. This assumption is exploited to achieve a reduction by a factor n in scan time, or an increase by n in temporal resolution (for segmented k-space scans), or some combination of the two. Although n can be arbitrarily large in theory, a choice n>2 would seem impractical in cardiac imaging. The dynamic heart and descending aorta tend to occupy roughly one half of the FOV in the anterior/posterior direction, essentially limiting the value of n to 2. The dynamic region, which is half the total FOV for n=2, can be placed anywhere in the reconstructed FOV at the post-processing stage (the position of the dynamic ½ FOV was adjusted to overlap the heart and aorta in the results presented in FIGS. 3 and 5).

The present method provides a way of calculating the value of some k-space data, acquired only once, for any phase in the cardiac cycle. If this data was used without the correction described by Eq. 2, the result would be a data set where the dynamic object (e.g. the heart) moves in a sluggish and non-natural way, with ghost artifacts (due to time inconsistencies among the various acquisitions making up the k-space matrix). On the other hand, the proposed algorithm can calculate a full k-space matrix at any time point in the cardiac cycle using only one $n^{th}$ of the data that would conventionally be required; this reduction in data requirements can be translated into either a decrease in imaging time or an improvement in temporal resolution. The trade-off for these improvements is a reduction in SNR, and potential artifacts if some material assumed static actually undergoes changes. These two points are discussed in the following two paragraphs, beginning with some SNR issues.

Consider a data set acquired with a conventional cine sequence. Using the same definition as in Appendix 1, the noise level in the reconstructed images is $\sigma_{ref}$. Suppose the chosen FOV is too small by a factor of 2 for the object, with half the object considered static (n=2). In such a situation, the present method can generate frames where the dynamic region is displayed with a noise level of up to (Eq. 5 with n=2). The static region is also displayed by the method, having a noise $0.79\sigma_{ref}$. In other words, if the static half simply did not exist, the dynamic object could have been imaged using a small FOV standard cine method, with a resulting noise $\sigma_{ref}$. The present method allows the object to be imaged using this same small FOV, and the aliasing created by the static portion is corrected for. This correction of the aliasing problem comes at the cost of an increased noise level over the dynamic part (between 27% and ~16% depending on cardiac phase, as shown in FIG. 4), and the static region is also visualized.

A second limitation of the present method comes from the assumption upon which it is built. If the material assumed to be static is indeed static, the present method represents an exact solution and no ghosting artifact is created. However, signal changes in the so-called static region would be interpreted by the algorithm as coming from material located in the dynamic region, and artifacts would be generated in the dynamic region. In our experience, the thoracic cage as well as the back can generally be assumed static if breath holding is used. The present method could prove useful, for example, in a cardiac imaging situation where a diminution by a factor two in imaging time would bring the scan time within breath holding range. Furthermore, it should prove valuable in some flow phantom experiments. In such experiments, tubes containing flowing water are often surrounded by static water; the assumption that part of the FOV is in fact static would then be especially appropriate.

The described invention is a reduced-FOV method designed to be compatible with cine imaging, and compatible with Cartesian and non-Cartesian (e.g. spiral) data sampling schemes. In the case where only one $n^{th}$ of the FOV is dynamic (the remainder of the FOV being considered static), the present method can improve temporal resolution or reduce scan time by a factor n.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

Appendix 1

This appendix compares the SNR of the present method to that of a reference case having the same imaging time. In this reference case, a FOV the size of the dynamic region would be acquired (potentially leading to images corrupted by aliasing), using a conventional cine sequence. The number of k-space acquisitions for the reference case is defined as $N_{rFOV}$, and the standard deviation due to noise in the image domain is $\sigma_{ref}$. Let's consider the noise for the case where a full-FOV image (non-aliased) would be acquired, as a function of $\sigma_{ref}$. Since there are more k-space acquisitions, (all contributing a same amount of noise), more noise should be present in the full-FOV image. On the other hand, more k-space acquisitions also means more signal. If we normalize to the signal, since the SNR in the full-FOV image is $\sqrt{n}$ higher than in the reference image, the noise has to be $\sqrt{n}$ lower ($\sigma_{ref}/\sqrt{n}$). Consider the noise in the full-FOV image as coming from n groups of $N_{rFOV}$ k-space acquisitions; each group contributes a standard deviation $\sigma_{ref}/n$, and these contributions add in quadrature to give $\sigma_{ref}/\sqrt{n}$. Furthermore, it is well known that the temporal interpolation involved in cine reconstruction reduces noise by a factor $\sqrt{3/2}$. Accordingly, a normal (non-cine) image reconstructed from $N_{rFOV}$ $k_y$ lines would have a noise $\sqrt{3/2}\sigma_{ref}$.

The following is a combination of Eq. 1 and Eq. 2, compressed into a single equation:

$$K_\phi(k_x, k_y, k_z) = (M_\phi(k_x, k_y, k_z) + h(M_\phi(k_x, k_y, k_z))) - \qquad (3)$$
$$h(M_{\phi'}(k_x, k_y, k_z)) + S(k_x, k_y, k_z)$$

where $K_\phi$ is the full k-space reconstructed at some cardiac phase $\phi$, $M_\phi$ and $M_{\phi'}$ are, respectively, obtained by temporally interpolating to $\phi$ and $\phi'$ all the $N_{rFOV}$ k-space portions acquired multiple times over a full cardiac cycle (the other k-space locations are filled with zeros), S is obtained by combining in one matrix all the $(n-1)N_{rFOV}$ k-space portions which have been acquired only a single time (instead of multiple times over a full cardiac cycle), and h( ) is an operator which interpolates $N_{rFOV}$ k-space portions to obtain the missing $(n-1)N_{rFOV}$ ones (using zero-padding or the method described in Appendix 2). (For Eq. 3 to hold, h ( ) must also replace with zeros the $N_{rFOV}$ k-space portions that were already present in the argument.) Since each one of the $(n-1)N_{rFOV}$ k-space portions acquired a single time is characterized by its own $\phi'$, $-h(M_{\phi'})$ actually represents a composite matrix built through $(n-1)N_{rFOV}$ repetitions of a process where a temporal interpolation at $\phi'$ is followed by a k-space interpolation and the selection of one k-space portion.

The noise from the term $(M_\phi + h(M_\phi))$ interpolated to fill a full k-space matrix made of $nN_{rFOV}$ portions. The resulting k-space can be imagined as n groups of $N_{rFOV}$ portions, each containing the same noise (standard deviation proportional to $\sigma_{ref}/n$) and the same signal equal to the normal signal multiplied by $1/n$). In the static part, these n versions of the same noise add destructively, and no noise is contributed by the term $(M_\phi + h(M_\phi))$ (as could be expected since this term is obtained by zero-filling the static region). However, these n versions of the same noise add constructively in the dynamic region (and produce a standard deviation proportional to $\sigma_{ref}$) The term $-h(M_{\phi'})$ has noise properties similar to $(M_\phi + h(M_\phi))$, except that one of the n groups of $N_{rFOV}$ lines is missing. As a result, the equivalent of one group is left non-cancelled in the static part (standard deviation proportional to $\sigma_{ref}/n$), while only $(n-1)$ contributions add constructively in the dynamic region (standard deviation proportional to $(n-1)\sigma_{ref}/n$). Using Eq. 3, the SNR properties of the present method in both the static and the dynamic parts of the FOV can be derived.

Static part

The static part occupies a fraction $(n-1)/n$ of the whole FOV. The $(n-1)$ groups of $N_{rFov}$ k-space acquisitions contained in the term $S(k_x, k_y, k_z)$ (in Eq. 3) contribute a noise $(\sqrt{(n-1)}/n)(\sqrt{3/2}\sigma_{ref})$, while $(M_\phi + h(M_\phi))$ does not contribute any noise over the static region, and the term $-h(M_{\phi'})$ contributes a noise proportional to $\sigma_{ref}/n$. To obtain the exact contribution of $-h(M_{\phi'})$, one must take into account the averaging involved in the temporal linear interpolation used to calculate $M_{\phi'}(k_x, k_y, k_z)$ For every k-space portion, two acquisitions are averaged with a weight b and $(1-b)$. Assuming all values of b are equiprobable over the interval from 0 to 1, the variance in the static part is given by:

$$\sigma_{static}^2 = \left( \frac{n-1}{n^2} + \frac{1}{n^2} \frac{\int_0^1 (b^2 + (1-b)^2) db}{\int_0^1 db} \right) \left( \frac{3}{2} \sigma_{ref}^2 \right) \qquad (4)$$

$$= \frac{3n-1}{2n^2} \sigma_{ref}^2$$

Note that the same $S(k_x, k_y, k_z)$ and $-h(M_{\phi'}(k_x, k_y, k_z))$ are used for all the reconstructed time frames; accordingly, even the noise (and not just the signal) in the reconstructed static section is time-independent.

Dynamic part

Figure 6A:
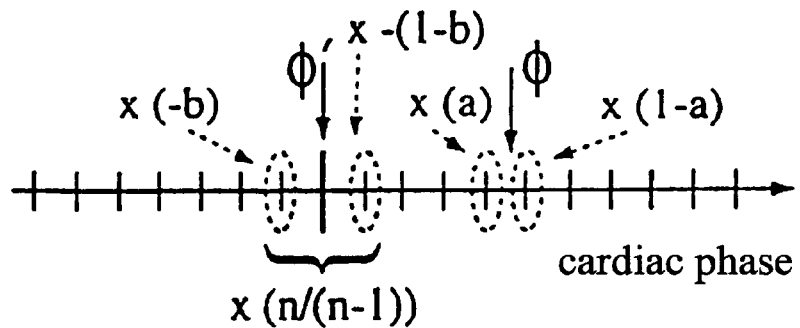
FIG. 6. illustrates k-space transfer of a portion of k-space data acquired at one cardiac phase to k-space data at another phase.

To transfer a k-space portion from the phase $\phi'$ where it has been acquired to the phase $\phi$ where a reconstructed frame is desired, one must interpolate the k-space portions acquired multiple times (over a full cardiac cycle) both at $\phi$ and $\phi'$. The noise properties of the dynamic portion depend on whether the two interpolations use common data. The case depicted in FIG. 6a is explored first. In this case, both acquisitions used for the linear interpolation at $\phi$ are different from the ones used at $\phi'$, for every transfer required to reconstruct a frame at $\phi$ (i.e. for all the $\phi'$ corresponding to different k-space portions acquired a single time). As in the static case, the term $S(k_x, k_y, k_z)$ contributes a standard deviation $(\sqrt{n-1}/n)(\sqrt{3/2}\sigma_{ref})$. As stated previously, the noise from the term $-h(M_{\phi'})$ is proportional to $(n-1)\sigma_{ref}/n$ in the dynamic region, while the noise from $(M_\phi + h(M_\phi))$ is proportional to $\sigma_{ref}$ Assuming that all values for the weights a and b involved in the temporal interpolation at $\phi$ and $\phi'$ are equiprobable over the interval from 0 to 1, the variance in the dynamic region is:

$$\sigma_{dyn1}^2 = \left( \frac{n-1}{n^2} + \frac{\int_0^1 \int_0^1 \left( a^2 + (1-a)^2 + \left(\frac{n-1}{n} b\right)^2 + \left(\frac{n-1}{n}(1-b)\right)^2 \right) da db}{\int_0^1 \int_0^1 da db} \right) \left( \frac{3}{2} \sigma_{ref}^2 \right) \qquad (5)$$

$$= \frac{4n^2 - n - 1}{2n^2} \sigma_{ref}^2$$

Figure 6B:
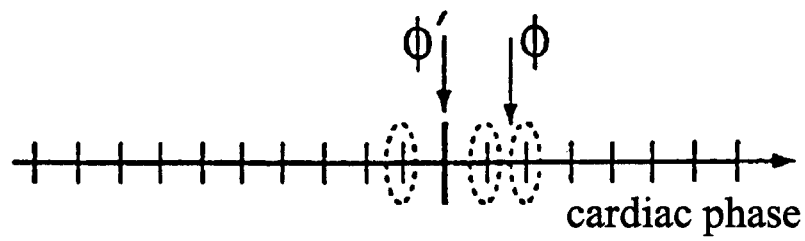

In the case depicted in FIG. 6b, one acquisition is shared between the interpolations at $\phi$ and $\phi'$, for every transfer required to reconstruct a frame at $\phi$. Still assuming a flat probability for a and b between 0 and 1, the variance in this second scenario is:

$$\sigma_{dyn2}^2 = \left( \frac{n-1}{n^2} + \frac{\int_0^1 \int_0^1 \left( a^2 + \left( (1-a) + \left( \frac{n-1}{n} b \right) \right)^2 \right) + \left( \frac{n-1}{n} (1-b) \right)^2 da\, db}{\int_0^1 \int_0^1 da\, db} \right) \left( \frac{3}{2} \sigma_{ref}^2 \right) \quad (6)$$

$$= \frac{5n^2 + n - 2}{4n^2} \sigma_{ref}^2$$

Figure 6C:
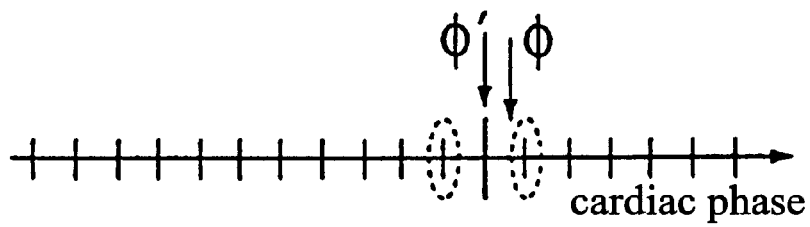

In the case depicted in FIG. 6c, both acquisitions are shared between the interpolation φ and at φ'. The variance in this third scenario is:

$$\sigma_{dyn3}^2 = \left( \frac{n-1}{n^2} + \frac{\int_0^1 \int_0^1 \left( \left( a - \left( \frac{n-1}{n} b \right) \right)^2 + \left( (1-a) - \left( \frac{(n-1)}{n} (1-b) \right) \right)^2 \right) da\, db}{\int_0^1 \int_0^1 da\, db} \right) \quad (7)$$

$$\left( \frac{3}{2} \sigma_{ref}^2 \right)$$

$$= \frac{n^2 + 2n - 1}{2n^2} \sigma_{ref}^2$$

In the extreme case where both interpolations would use the same two acquisitions with a same weighting factor (Eq. 7 with a=b), the variance is given by:

$$\sigma_{lim}^2 = \left( \frac{n-1}{n^2} + \frac{\int_0^1 \left( a^2 + (1-a)^2 \right) \left( 1 - \frac{n-1}{n} \right)^2 da}{\int_0^1 da} \right) \quad (8)$$

$$\left( \frac{3}{2} \sigma_{ref}^2 \right)$$

$$\frac{3n-1}{2n^2} \sigma_{ref}^2$$

In the limit case described by Eq. 8, the noise variance in the dynamic region is the same as in the static region (Eq. 4). However, in actual images, more noise is expected in the dynamic part. Chances are that some k-space portions are acquired at a phase φ' such that no common data is used in the interpolation at φ and 100 ' (as depicted in FIG. 6a), while some others are acquired at a phase φ' as depicted in FIG. 6b or c. Accordingly, the noise variance in the dynamic part is given by a combination of Eqs 5, 6 and 7:

$$\sigma_{dyn}^2 = (P_1 \sigma_{dyn1}^2 + P_2 \sigma_{dyn2}^2 + P_3 \sigma_{dyn3}^2) \quad (9)$$

The weighting factors $P_1$, $P_2$ and $P_3$ are the probabilities that the phases φ (where a frame is reconstructed) and φ' (where a k-space portion to be 'transferred' to φ has been acquired) are related to each other in a way depicted, respectively, by FIG. 6a, b or c ($P_1+P_2+P_3=1$). Some explanations about the values of $P_1$, $P_2$ and $P_3$ are presented in the following paragraph.

Consider a given k-space portion, acquired repeatedly over a full cardiac cycle. With the present method, (n−1) of these time points are replaced by the acquisition of a different k-space portion. There is some freedom in deciding which time point(s) are to be replaced in such fashion. In the proposed implementation, the first few time points after the R-wave are not replaced (in order to depict systole as well as possible). Accordingly, for the first reconstructed frames, the phase φ cannot be close to the phase φ' where replacements occur ($P_1=1$, $P_2=0$, $P_3=0$), and the noise in the dynamic part of these early frames is $\sigma_{dyn1}$ (Eq. 5). A similar situation arises for the late frames. To avoid the situation where an early R-wave would signal the end of the heartbeat before the needed replacement(s) are performed, no replacement is scheduled for high cardiac phase values; similarly to early phases, the dynamic part of frames reconstructed at late phases are characterized by a noise $\sigma_{dyn1}$. Suppose that N time points are acquired in the remaining intermediate cardiac phases, in a typical heartbeat. All of these N acquisitions are given the same probability of being replaced, and this decision is made independently for each one of the $N_{rFOV}$ dynamic acquisitions of a k-space portion. For the case n=2 presented in this paper, FIG. 7 shows that a frame reconstructed at an intermediate cardiac phase φ is expected to have a fraction 2/N of its 'transfers' from φ' to φ to be similar to the case depicted in FIG. 6c ($P_3=2/N$), a fraction 2/N similar to FIG. 6b ($P_2=2/N$), and a fraction (N−4)/N similar to FIG. 6a ($P_1=(N-4)/N$) (these values for $P_1$, $P_2$ and $P_3$ assume N≥4 and n =2). As a result, the expected noise in the dynamic region of a frame at an intermediate cardiac phase is (from Eq. 5, 6, 7 and 9):

$$\sigma_{dyn}^2 = \left( \frac{13N - 18}{8N} \right) \sigma_{ref}^2 \quad (10)$$

In summary, with the proposed implementation, the noise variance in the dynamic part of frames reconstructed at early or late cardiac phases is given by Eq. 5. On the other hand, a lower noise level is expected for intermediate cardiac phases, as described by Eq. 10 for the case n=2 (note that Eq. 10 becomes equivalent to Eq. 5 for a large N). Transition bands can be expected where the dynamic part of reconstructed frames has an intermediate noise level, making a smooth transition between early, intermediate and late cardiac phrases.

Appendix 2

This appendix presents a way of interpolating a k-space matrix sampled using spiral trajectories. Suppose that $S_{even}$ represents a set of spiral trajectories providing a FOV having a radius R/2 in the object domain. $S_{odd}$ is a second set of spiral trajectories, such that $S_{even}$ and $S_{odd}$ can be combined to provide a FOV having a radius R ($S_{odd}$ consists of spirals that are interleaved with the spirals in $S_{even}$). Suppose that, as with the present method, one wants to calculate the value of data on a given spiral trajectory within the set $S_{odd}$ through an interpolation of the known set $S_{even}$.

In a first step, the whole set $S_{odd}$ can be interpolated from a known $S_{even}$ in the following way. A set $S_{odd}$ of spirals, simply filled with zeros, is generated and combined with the (known) set $S_{even}$ (which contains the measured data). This data set is gridded and inverse-FFTed to the object domain. The resulting image is left unchanged over half the radius of the FOV (a disk of radius R/2) while every voxel outside this unmodified disk has its phase shifted by 180°. After an FFT, the result is in fact a (gridded) k-space matrix where the spiral trajectories that belong to $S_{even}$ are filled with zeros, while the ones part of $S_{odd}$ are filled with (interpolated) data.

The various spiral trajectories in $S_{odd}$ may, due to the convolution with the gridding kernel, partly overlap with each other. The following approximation was made to allow the extraction of a given spiral $i_o$ from the whole interpolated set. Imagine a situation where all the spiral trajectories in $S_{odd}$ would be filled with ones, and then gridded through convolution with a kernel. In this case, one can calculate what fraction of the signal is due to the spiral trajectory $i_o$, at any point in the k-space matrix. The resulting map of weighting factors is used to extract an approximation of spiral the $i_o$ from an interpolated set $S_{odd}$.

The present algorithm was chosen over other possibilities because it does not involve prohibitively time consuming operations such as convolution with a large kernel or discrete FT. A exact solution could be used to extract a single, interpolated spiral trajectory , but the reconstruction time would be longer.

Appendix 3

The following algorithm is proposed to efficiently implement the present method:

1. For all the k-space portions acquired a single time at some phase φ':
   (a) Store the k-space portion into a matrix S.
   (b) Interpolate to phase φ' the portions acquired multiple times.
   (c) Interpolate the result (in k-space), and store the k-space portion under consideration into a matrix $h(M_{\phi'})$.

2. Then, for all the phases φ where a reconstructed frame is desired:
   (a) Interpolate to φ the portions acquired multiple times and save the result into $M_\phi$.
   (b) Interpolate (in k-space) to fill the parts left empty in $M_\phi$, using FFT-(zero-filling)-inverse FFT (for a Cartesian acquisition) or the method in Appendix 1 (for a spiral acquisition), and store the result in a matrix $h(M_\phi)$.
   (c) Calculate the reconstructed frame through Eq. 3.

Note that in step 1(c) for the Cartesian case, the interpolation can be performed faster using a convolution with a sinc function than with an FFT-(zero-padding)-inverse FFT operation. Since only one $k_y$ line is needed from the result of the interpolation, it is faster to calculate only this line using a 1D convolution along $k_y$ than to FFT a matrix, zero-pad, inverse FFT a matrix and then select only one line in the result.

References

[1] Joseph A. Utz, Robert J. Herfkens, James A. Heinsimer, Thomas Bashore, Robert Califf, Gary Glover, Norbert Pelc, and Ann Shimakawa. Cine MR determination of left ventricular ejection fraction. *Am J Roentgenol*, 148:839–843, 1987.

[2] Gerald W. Lenz, E. Mark Haacke, and Richard D. White. Retrospective cardiac gating: a review of technical aspects and future directions. *Magn Reson Imaging*, 7:445–455, 1989.

[3] Seiji Ogawa, T. M. Lee, A. R. Kay, and D. W. Tank. Brain magnetic resonance imaging with contrast dependent on blood oxygenation. *Proc. Natl. Acad. Sci. USA*, 87:9868–9872, 1990.

[4] Bruce R. Rosen, John W. Belliveau, James M. Vevea, and Thomas J. Brady. Perfusion imaging with NMR contrast agents. *Magn Reson Med*, 14:249–265, 1990.

[5] Walter G. O'Dell, Christopher C. Moore, William C. Hunter, Elias A. Zerhotuni, and Elliot R. McVeigh. Three-dimensional myocardial deformations: Calculation with displacement field fitting to tagged MR images. *Radiology*, 195:829–835, 1995.

[6] Frank R. Korosec, Richard Frayne, Thomas M. Grist, and Charles A. Mistretta. Time-resolved contrast-enhanced 3D MR angiography. *Magn Reson Med*, 36:345–351, 1996.

[7] R. Fransen, H-J. Muller, W. H. Boer, K. Nicolay, and H. A. Koomans. Contrast-enhanced dynamic magnetic resonance imaging of the rat kidney. *J Am Soc Nephrol*, 7:424–430, 1996.

[8] S. Mussurakis, D. L. Buckley, P. J. Drew, J. N. Fox, P. J. Carletoii, L. V. Turnbull, and A. Horsman. Dynamic MR imaging of the breast combined with analysis of contrast agent kinetics in the differentiation of primary breast tumours. *Clin Radiol*, 52:516–526, 1997.

[9] Xiaoping Hu and Todd Parrish. Reduction of field of view for dynamic imaging. *Magn Reson Med*, 31:691–694, 1994.

[10] Walid E. Kyriakos, Lawrence P. Panych, Gary P. Zientara, and Ferenc A. Jolesz. Implementation of a reduced field-of-view method for dynamic MR imaging using navigator echoes. *J Magn Reson Imaging*, 7:376–381, 1997.

[11] Jill O. Fredrickson and Norbert J. Pelc. Temporal resolution improvement in dynamic imaging. *Magn Reson Med*, 35:621–625, 1996.

[12] Bruno Madore, Gary H. Glover, and Norbert J. Pelc. UNaliasing by Fourier-encoding the Overlaps using the temporal Dimension (UNFOLD), applied to cardiac imaging and fMRI. To be published.

[13] D. R. Bailes, D. J. Gilderdale, G. M. Bydder, A. G. Collins, and D. N. Firmin. Respiratory ordering of phase encoding (ROPE): a method for reducing respiratory motion artifacts in MR imaging. *J Comput Assist Tomogr*, 9:835–838, 1985.

[14] Norbert J. Pelc and Gary H. Glover. Method of reducing image artifacts due to periodic signal variations in NMR imaging. U.S. Pat. No. 4,663,591. Filed Aug. 16, 1985, issued May 5, 1987.

[15] Marcus T. Alley, Norbert J. Pelc, and Robert J. Herfens. A fast 3D-cine acquisition for cardiac imaging. In *ISMRM proceedings*, page 907,Vancouver, Canada, 1997.

[16] Jan Ray Liao, F. Graham Sommer, Robert J. Herfkens, and Norbert J. Pelc. Cine spiral imaging. *Magn Reson Med*, 34:490–493, 1995.

What is claimed is:

1. A method of imaging an object having both dynamic and static portions in a field of view during a motion cycle where the dynamic portion is 1/n of the total field of view, the method using spatial encoding of MRI signals wherein each signal is characterized by a spatial encoding parameter and wherein the MRI signals contain information about both static and dynamic portions of the field of view, the method comprising the steps of:

a) acquiring a first set of MRI signals, said set comprised of at least one subset, each subset being comprised of signals acquired with the same spatial encoding parameters, wherein the elements of each subset were acquired at a plurality of time points spanning the entire motion cycle, said first set being characterized by a first set of spatial encoding parameters sufficient to portray 1/n of the full field of view, where n is greater than one, b) acquiring a second set of MRI signals, said second set comprised of at least one subset, each comprised of signals acquired with the same spatial encoding parameters, wherein the elements of each subset do not span the entire motion cycle, wherein the various subsets are acquired at substantially different time points in the motion cycle, said second set being characterized by a second set of spatial encoding parameters, and wherein said first set of encoding parameters together with said second set of encoding parameters are sufficient to portray the full field of view, c) generating MRI signals for a plurality of time points spanning an entire motion cycle for the spatial encoding parameters of the first set of MRI signals and of the second set of MRI signals using the acquired first MRI signals and the acquired second MRI signals, and d) producing images of at least a portion of the object at the plurality of time points using the generated MRI signals.

2. A method of imaging an object having both dynamic and static portions in a field of view during a motion cycle where the dynamic portion is 1/n of the full field of view, the method comprising the steps of:

a) acquiring a first set of MRI signals, said set comprised of at least one subset, each subset being comprised of signals acquired with the same spatial encoding parameters, wherein the elements of each subset were acquired at a plurality of time points spanning the entire motion cycle, said first set being characterized by a first set of spatial encoding parameters sufficient to portray 1/n of the full field of view, where n is greater than one, b) acquiring a second set of MRI signals, said second set comprised of at least one subset, each comprised of signals acquired with the same spatial encoding parameters, wherein the elements of each subset do not span the entire motion cycle, wherein the various subsets are acquired at substantially different time points in the motion cycle, said second set being characterized by a second set of spatial encoding parameters, and wherein said first set of encoding parameters together with said second set of encoding parameters are sufficient to portray the full field of view, and c) producing an image of at least a portion of the object at the said desired time using the generated MRI signals.

3. The method as defined by claim 1 wherein generated MRI signals at a given time point include the first set of MRI signals acquired at substantially the given time point and information from the second set of MRI signals acquired at other time points and transferred to the given time point.

4. The method of claim 3 wherein step c) includes the steps of:

c1) computing, for at least a subset of the first set of spatial encoding parameters, data for the change in the dynamic region:

$$\Delta_n(k_x,k_y)=K_n(k_x,k_y)-K_n'(k_x,k_y)$$

wherein $K_n$ and $K_n'$ represent, respectively, the first MRI signals at the given time point $\phi$ at the time point $\phi'$ at which a particular second MRI signal was acquired, c2) using $\Delta_n(k_{x,y})$ from step c1) to estimate signal $\Delta$ for the change in the dynamic portion for the spatial encoding parameter measured at time $\phi'$, and c3) generating MRI signal for the object at time $\phi$ by adding $\Delta$ from step c2) to the second MRI signal measured at time $\phi'$.

5. The method as defined by claim 4 wherein the MRI signals are samples of the Fourier transform of the object on a Cartesian grid.

6. The method as defined by claim 4 wherein the MRI signals are samples of the Fourier transform of the object along spiral paths.

7. The method as defined by claim 4 wherein the object is a heart and the motion cycle is a cardiac cycle.

8. The method as defined by claim 7 wherein n is 2.

9. The method as defined by claim 1 wherein the object is a heart and the motion cycle is a cardiac cycle.

10. The method as defined by claim 9 wherein n is 2.

11. The method of claim 2 further including d) repeating step b)–c) at a plurality of desired times.

12. The method as defined by claim 11 wherein step b) includes transferring a k space scan line acquired at time $\phi'$ to the desired time $\phi$ by adding to the measured other k space scan line at $\phi'$ a difference, $\Delta$, between the first set of MRI signals for time $\phi$ and the first set of MRI signals for time $\phi'$.

13. The method as defined by claim 11 wherein the object is a heart and the motion cycle is a cardiac cycle.

14. The method as defined by claim 12 wherein n is 2.

15. The method as defined by claim 2 wherein the object is a heart and the motion cycle is a cardiac cycle.

16. The method as defined by claim 14 wherein n is 2.

17. The method as defined by claim 2 wherein images with two spatial dimensions are produced.

18. The method as defined by claim 2 wherein images with three spatial dimensions are produced.

* * * * *